(12) United States Patent
Kim et al.

(10) Patent No.: US 11,596,836 B2
(45) Date of Patent: Mar. 7, 2023

(54) DISPLAY APPARATUS AND METHOD OF CONTROLLING THE SAME FOR VISUALIZING BODY CHANGES

(71) Applicants: Hyundai Motor Company, Seoul (KR); Kia Motors Corporation, Seoul (KR)

(72) Inventors: Sung Un Kim, Gyeonggi-do (KR); Jeongwoo Nahm, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 17/108,407

(22) Filed: Dec. 1, 2020

(65) Prior Publication Data

US 2021/0308526 A1 Oct. 7, 2021

(30) Foreign Application Priority Data

Apr. 6, 2020 (KR) ........................ 10-2020-0041421

(51) Int. Cl.
| | |
|---|---|
| *A63B 24/00* | (2006.01) |
| *G06F 3/0488* | (2022.01) |
| *G06F 3/0482* | (2013.01) |
| *G06V 40/10* | (2022.01) |

(52) U.S. Cl.
CPC ........ *A63B 24/0075* (2013.01); *G06F 3/0482* (2013.01); *G06F 3/0488* (2013.01); *G06V 40/103* (2022.01); *A63B 2230/00* (2013.01); *A63B 2230/01* (2013.01); *A63B 2230/015* (2013.01); *A63B 2230/60* (2013.01); *A63B 2230/605* (2013.01); *A63B 2230/70* (2013.01); *A63B 2230/705* (2013.01)

(58) Field of Classification Search
CPC ...... G06V 40/70; G06V 40/10; G06V 40/103; A63B 2230/00; A63B 2230/01; A63B 2230/015; A63B 2230/60; A63B 2230/605; A63B 2230/70; A63B 2230/705; A63B 24/0075; G06F 3/0482; G06F 3/0488

See application file for complete search history.

(56) References Cited

U.S. PATENT DOCUMENTS

| | | | | |
|---|---|---|---|---|
| 9,984,588 | B1 * | 5/2018 | Barker | ................ G06V 40/103 |
| 2003/0108851 | A1 * | 6/2003 | Posa | .................. G09B 19/0076 |
| | | | | 434/118 |
| 2004/0131227 | A1 * | 7/2004 | Bravomalo | ........ G06Q 30/0269 |
| | | | | 382/100 |
| 2008/0270890 | A1 * | 10/2008 | Stern | .................... G06F 16/9577 |
| | | | | 707/999.102 |

(Continued)

*Primary Examiner* — Daniel Samwel
(74) *Attorney, Agent, or Firm* — Fox Rothschild LLP

(57) ABSTRACT

A display apparatus includes a controller for obtaining image information using an image obtainer; obtaining body images of a user based on the received image information; receiving menu information of at least one of a somatotype mode or an exercise purpose through an inputter; obtaining parameters for each part of a body based on the obtained body image; adjusting at least one of the obtained parameters for each part of the body based on the received menu information; changing an image for each part of the body among the body images based on the adjusted parameter; and displaying the changed image through a screen.

12 Claims, 10 Drawing Sheets

(56) References Cited

U.S. PATENT DOCUMENTS

| | | | | |
|---|---|---|---|---|
| 2013/0120445 A1* | 5/2013 | Shimomura | .......... | G02B 27/017 345/629 |
| 2014/0340479 A1* | 11/2014 | Moore | .................... | G06T 17/20 348/43 |
| 2014/0347479 A1* | 11/2014 | Givon | .................. | G06V 40/103 382/116 |

* cited by examiner

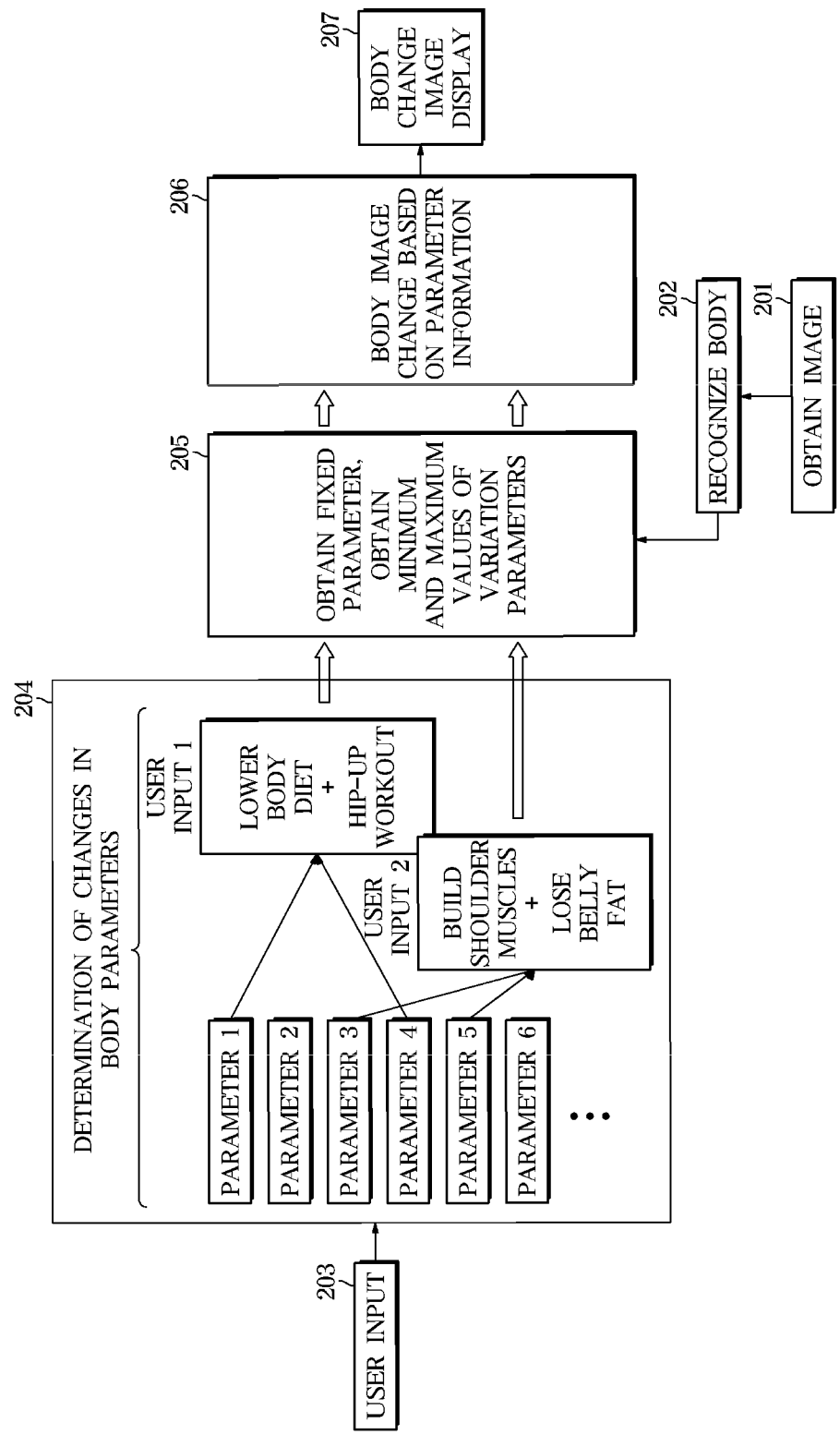

DISPLAY APPARATUS AND METHOD OF CONTROLLING THE SAME FOR VISUALIZING BODY CHANGES

CROSS-REFERENCE TO RELATED APPLICATION(S)

This application claims under 35 U.S.C. § 119 the benefit of Korean Patent Application No. 10-2020-0041421, filed on Apr. 6, 2020 in the Korean Intellectual Property Office, the entire contents of which are incorporated by reference herein.

BACKGROUND

(a) Technical Field

The disclosure relates to an image processing apparatus for obtaining an external image and storing and displaying the obtained image, a vehicle having the same, and a method of controlling a display apparatus.

(b) Description of the Related Art

A human body often suffers from body imbalance because front, rear, left, and right sides of the body are not balanced correctly due to incorrect posture, underlying medical conditions, etc. For example, when a user sits at a desk for a long time and uses a computer, or when the user sits for a long time with incorrect or poor posture while driving, body imbalance may result. In addition, if a person's right leg suffers from a disease or pain and causes the person to favor a left leg for a long time, the left and right sides of the body may not be balanced, resulting in body imbalance.

When body imbalance is left unattended for a long period of time, since it may have an adverse effect on health, equipment has been developed to analyze a somatotype, body balance, and health status.

In a somatotype analysis of the human body, an angle of an ankle is measured from a rear to observe whether it is valgus or varus, or this type of analysis is used to determine whether a person has an O-shaped leg or an X-shaped leg by comparing a gap between a knee and the ankle. More specifically, the somatotype is analyzed by considering a whole body side and a degree of inclination leading to a shoulder, a pelvis, the knee, and the ankle based on a base of an ear, or is analyzed by calculating a degree of inclination leading to left and right shoulders, the pelvis, and the knee based on a center of a head, looking at the rear of the whole body.

However, a conventional somatotype analysis device simply measures the user's height and weight, measures body fat through bioelectrical impedance, and provides results based on this. This method has a problem in that it does not provide accurate detailed data on the somatotype or posture of the user because measurement data itself has limitations.

In addition, in the analysis method, since the captured image is based on a viewer's perspective and subjective evaluation, there are disadvantages that may lead to different results, and there is also a disadvantage that it is impossible to provide information about results that take into account the role of exercise.

SUMMARY

An aspect of the disclosure is to provide a display apparatus that obtains a user's body image and displays information about changes to the user's body image based on the obtained body image and a user input, and a method of controlling the display apparatus.

Another aspect of the disclosure is to provide a display apparatus that analyzes a somatotype based on the user's body image and guides exercise information based on the analyzed somatotype, and a method of controlling the display apparatus.

Additional aspects of the disclosure will be set forth in part in the description which follows and, in part, will be obvious from the description, or may be learned by practice of the disclosure.

In accordance with an aspect of the disclosure, a display apparatus includes a communicator configured to receive image information about an image obtained by an image obtainer; an inputter configured to receive menu information of at least one of a somatotype mode or an exercise purpose; a controller configured to obtain body images of a user based on the received image information, to obtain parameters for each part of a body based on the obtained body image, to adjust at least one of the obtained parameters for each part of the body based on the received menu information, and to change an image for each part of the body among the body images based on the adjusted parameter; and a screen configured to display the changed image in response to a control command of the controller.

The controller may be configured to recognize joints based on the obtained body image when obtaining parameters for each part of the body; obtain position information of the recognized joints based on the obtained body image; and obtain a first parameter for each part of the user's body based on the obtained position information of the joints.

The controller may be configured to obtain a second parameter for each part of the body corresponding to the somatotype mode and the exercise purpose when adjusting at least one of the obtained parameters for each part of the body; determine a change value of the parameter for each part of the body based on the obtained first and second parameters for each part of the body; and adjust at least one of the obtained parameters for each part of the body based on the determined change value of the parameter for each part of the body.

The controller may be configured to generate a distance between the recognized joints as a fixed parameter when adjusting at least one of the obtained parameters for each part of the body; generate a width and circumference of the part between the recognized joints and a width and circumference of the joints as variation parameters; and adjust at least one of the obtained parameters for each part of the body based on the generated variation parameters.

The display apparatus may further include a storage configured to store information about maximum and minimum values of the variation parameters for each fixed parameter and a height of the user. The controller may be configured to obtain the maximum and minimum values of the variation parameters based on the information stored in the storage and the user's body information; and to adjust at least one of the obtained parameters for each part of the body based on the determined change value of the parameter for each part of the body and the maximum and minimum values of the obtained variation parameters.

The controller may be configured to obtain an increase or decrease of the first parameter for each part of the user's body based on the determined change value of the parameter for each part of the body and the maximum and minimum values of the obtained variation parameters; and perform erosion image processing or dilation image processing for each part of the determined body based on the obtained increase or decrease of the first parameter for each part of the user's body.

The controller may be configured to obtain an increase or decrease of the first parameter for each part of the user's body based on the determined change value of the parameter for each part of the body and the maximum and minimum values of the obtained variation parameters; identify the number of pixels corresponding to the increase or decrease of the first parameter for each part of the user's body; and perform erosion image processing or dilation image processing for each part of the determined body based on the identified number of pixels.

The controller may be configured to perform the erosion image processing or the dilation image processing in a direction perpendicular to a direction in which the joints are connected.

The controller may be configured to generate a body change image reflecting the changed image of each part of the body; change left and right portions of the generated body change image; and control the screen to display the body change image with the left and right portions changed.

The controller may be configured to control the screen to display the obtained body image and the body change image overlaid.

The inputter may be configured to receive at least one exercise information among an exercise type, an exercise time, or an exercise intensity. The controller may be configured to adjust at least one of the obtained parameters for each part of the body based on the received exercise information.

The image obtainer is integrally provided with the screen.

The inputter may include a touch panel. The screen may include a display panel provided on one side of the touch panel.

In accordance with another aspect of the disclosure, a method of controlling a display apparatus includes obtaining image information using an image obtainer; obtaining body images of a user based on the received image information; receiving menu information of at least one of a somatotype mode or an exercise purpose through an inputter; obtaining parameters for each part of a body based on the obtained body image; adjusting at least one of the obtained parameters for each part of the body based on the received menu information; changing an image for each part of the body among the body images based on the adjusted parameter; and displaying the changed image through a screen.

The adjusting of the at least one of the obtained parameters for each part of the body may include recognizing joints based on the obtained body image; obtaining position information of the recognized joints based on the obtained body image; obtaining a first parameter for each part of the user's body based on the obtained position information of the joints; obtaining a second parameter for each part of the body corresponding to the somatotype mode and the exercise purpose; determining a change value of the parameter for each part of the body based on the obtained first and second parameters for each part of the body; and adjusting at least one of the obtained parameters for each part of the body based on the determined change value of the parameter for each part of the body.

The adjusting of the at least one of the obtained parameters for each part of the body may include generating a distance between the recognized joints as a fixed parameter; generating a width and circumference of the part between the recognized joints and a width and circumference of the joints as variation parameters; and adjusting at least one of the obtained parameters for each part of the body based on the generated variation parameters.

The changing of the image based on the adjusted parameter may include obtaining the maximum and minimum values of the variation parameters based on information stored in a storage and the user's body information; obtaining an increase or decrease of the first parameter for each part of the user's body based on the determined change value of the parameter for each part of the body and the maximum and minimum values of the obtained variation parameters; and performing erosion image processing or dilation image processing for each part of the determined body based on the obtained increase or decrease of the first parameter for each part of the user's body. The information stored in the storage may include information about maximum and minimum values of the variation parameters for each fixed parameter and a height of the user.

The performing of the erosion image processing or the dilation image processing for each part of the determined body may include identifying the number of pixels corresponding to the increase or decrease of the first parameter for each part of the user's body; and performing the erosion image processing or the dilation image processing for each part of the determined body based on the identified number of pixels, but performing the erosion image processing or the dilation image processing in a direction perpendicular to a direction in which the joints are connected.

The method may further include generating a body change image reflecting the changed image of each part of the body; changing left and right portions of the generated body change image; and controlling the screen to display the body change image with the left and right portions changed on the obtained body image.

The method may further include adjusting at least one of the obtained parameters for each part of the body based on the received exercise information when at least one exercise information among an exercise type, an exercise time, and an exercise intensity is received through the inputter.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 6 is a control flowchart of a display apparatus according to an embodiment.

DETAILED DESCRIPTION

Figure 1:
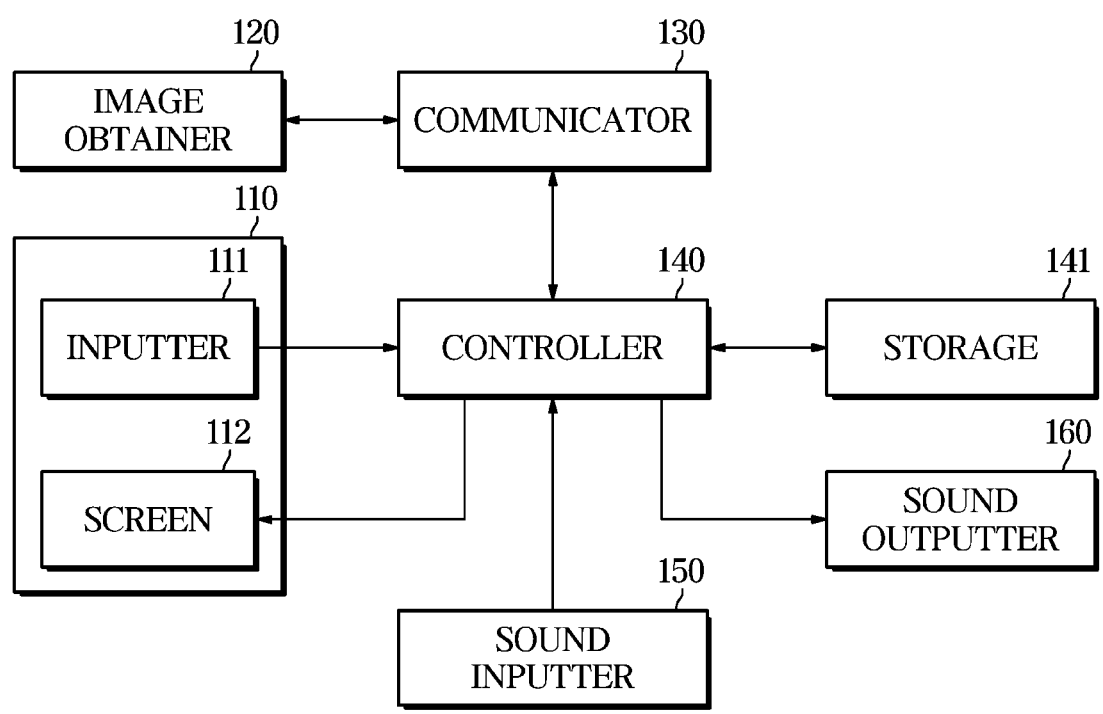
FIG. 1 is a control configuration diagram of a display apparatus according to an embodiment.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Like reference numerals refer to like elements throughout the specification. Not all elements of the embodiments of the disclosure will be described, and the description of what are commonly known in the art or what overlap each other in the exemplary embodiments will be omitted. It will be further understood that the term "connect" and its derivatives refer both to direct and indirect connection, and the indirect connection includes a connection over a wireless communication network.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

Reference numerals used for method steps are merely used for convenience of explanation, but not to limit an order of the steps. Thus, unless the context clearly dictates otherwise, the written order may be practiced otherwise.

Hereinafter, an operation principle and embodiments of the disclosure will be described with reference to accompanying drawings.

Figure 2:
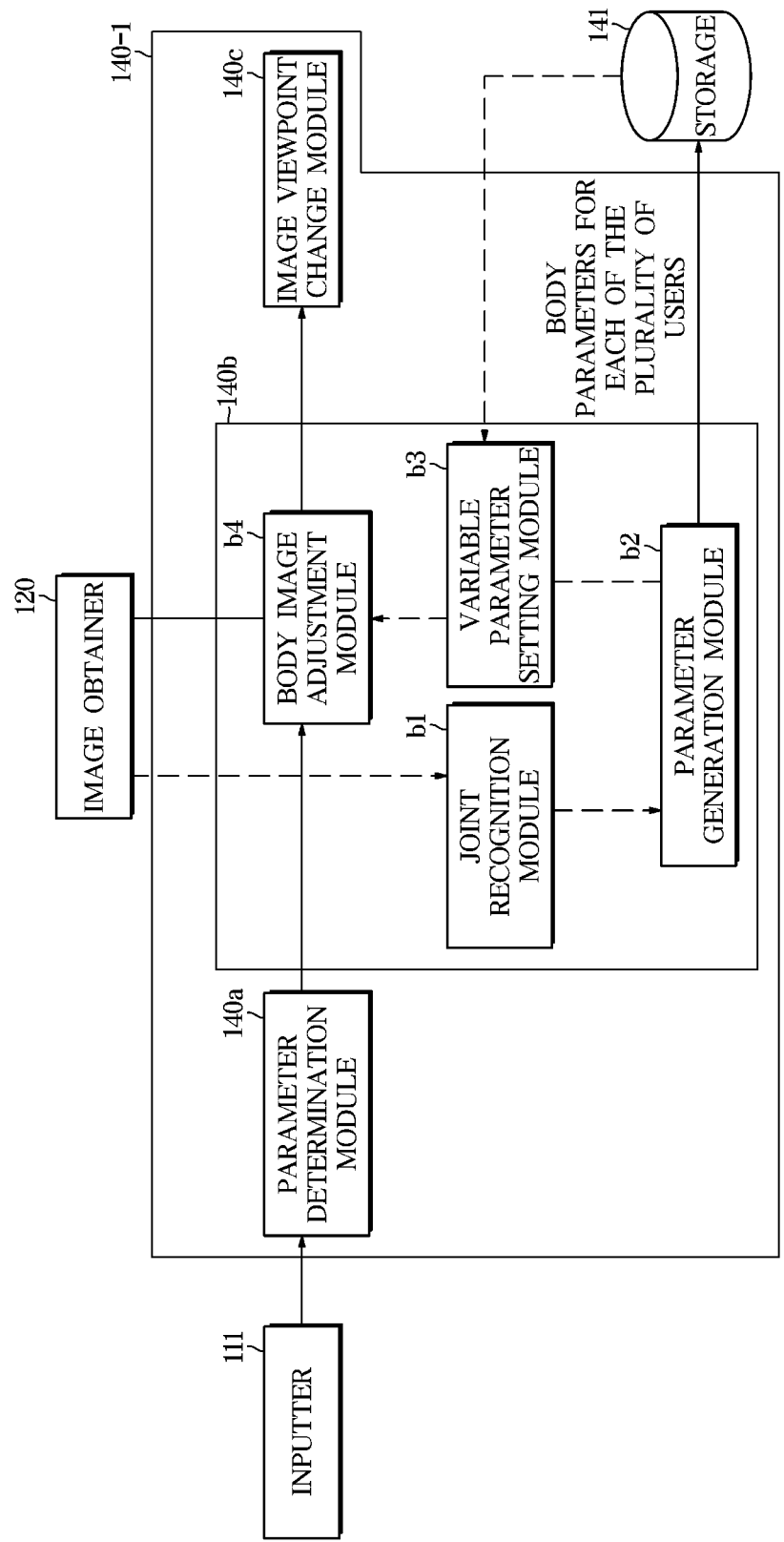
FIG. 2 is a detailed configuration diagram of a controller illustrated in FIG. 1.

FIG. 1 is a control configuration diagram of a display apparatus according to an embodiment, and FIG. 2 is a detailed configuration diagram of a controller illustrated in FIG. 1.

A display apparatus 1 includes a user interface 110, an image obtainer 120, a communicator 130, a controller 140, a storage 141, a sound inputter 150, and a sound outputter 160.

The user interface 110 may include an inputter 111 for receiving a user input, and a screen 112 displaying various information as an image so that the user can visually identify the user input.

Here, the user input may include a power command corresponding to an on command or an off command, a scan command, and an output command of exercise information.

In addition, the user input may include a selection command of at least one menu among a plurality of menus, an output command of an exercise guide, and the like.

The menu may include a somatotype mode, an exercise purpose, a guidance of results, and the like.

The somatotype mode is a skinny mode, a standard somatotype mode, a sports model mode, a bodybuilder mode, and the like.

The exercise purpose may include diet, musculoskeletal disease, muscle strengthening, somatotype correction, muscle strength enhancement, muscle endurance enhancement, flexibility enhancement, aerobic enhancement, weight control, cardiovascular health, cancer prevention, bone density loss prevention, diabetes control, psychological benefits, and self-esteem.

The inputter 111 may select an exercise type, an exercise intensity, an exercise time, etc. for each exercise purpose.

The inputter 111 may receive guide commands such as exercise methods and precautions for each exercise type.

The inputter 111 may include a touch panel, and may include a plurality of buttons.

The inputter 111 may further include a jog dial or a touch pad for inputting a movement command and a selection command of a cursor displayed on the screen 112.

The inputter 111 may receive identification information of the user.

The identification information of the user may include information about the user's name, the user's ID, and the user's age.

The inputter 111 may also receive body information about the height and weight of the user.

The screen 112 may display information of various functions that can be performed in the display apparatus 1 and information of various functions that are being performed in the display apparatus 1, and may display information input by the user.

The screen 112 may display the body image obtained by the image obtainer 120 in response to a control command of the controller 140.

The screen 112 may display a past body image and a current body image, and display a comparison image between the past body image and the current body image.

The screen 112 may display a realistic image (that is, a nude image) in response to the command from the controller 140, or may display a body image covered by a preset region, and may display a border image corresponding to the nude image.

The screen 112 may display a somatotype change image in response to the control command of the controller 140.

The screen 112 may simultaneously display somatotype change images corresponding to a plurality of somatotype modes on a single screen.

The plurality of somatotype modes may include the skinny mode, the sports model mode, the bodybuilder mode, and the standard somatotype mode.

The screen 112 may display the exercise information corresponding to the somatotype mode or the exercise purpose.

The exercise information may include the exercise type, the exercise intensity, the exercise time, the exercise methods, the precautions, and the like.

The exercise type may include aerobic exercise, isometric exercise, isotonic exercise, isokinetic exercise, and anaerobic exercise.

The exercise type may also include detailed types of exercise, such as flanks, side flanks, bridges, and one-leg gluten bridges.

The screen 112 may display a single still image or a video.

The screen 112 may also include a mirror and a display panel.

The screen 112 may perform a mirror function. The screen 112 may display the body image of the real image through the mirror function, or may display the changed somatotype body image through the mirror function.

When the body image is displayed, the screen 112 may change and display the left and right portions of the body image from a viewpoint of the image obtainer (i.e., the camera) to a viewpoint of the user's eye.

The screen 112 may be implemented through the display panel.

The user interface 110 may be provided as a touch screen in which the touch panel is integrated in the display panel.

The inputter 111 and the screen 112 may be provided separately from each other. In this case, the inputter 111 and the screen 112 may be connected through wired communication or wireless communication.

The image obtainer 120 may obtain surrounding images.

The image obtainer 120 may obtain the image in real time. That is, the image obtainer 130 may obtain the image of the video.

The image obtainer 120 is a camera that converts shape information about surrounding objects into electrical image signals, and may transmit image signals corresponding to shape information of the user's body to the controller 140.

The image obtainer 120 may include a charge-coupled device (CCD) or a complimentary metal-oxide semiconductor (CMOS) image sensor and may include a 3D spatial recognition sensor such as a KINECT (RGB-D Sensor), a TOF (Structured Light Sensor), a stereo camera, and the like.

The image obtainer 120 may include one or more cameras.

The image obtainer 120 may include a rotatable camera.

The image obtainer 120 may be provided separately from the screen 112 and may be provided around the screen, or may be integrally provided with the screen 112.

The image obtainer 120 may perform wired or wireless communication with the controller 140.

The communicator 130 may be configured to perform communication between various components of the display apparatus 1, communication with an external device, communication with a user terminal, and communication with a storage medium.

The communicator 130 may include one or more components that enable communication with the controller 140, for example, at least one of a short-range communication module, a wired communication module, or a wireless communication module.

The short-range communication module may include various short-range communication modules for transmitting and receiving signals within a short range over a wireless communication network, such as a Bluetooth module, an infrared communication module, a radio frequency identification (RFID) communication module, a wireless local access network (WLAN) communication module, a near field communication (NFC) module, a Zigbee communication module, etc.

The wired communication module may include not only one of the various wired communication modules, such as a controller area network (CAN) communication module, a local area network (LAN) module, a wide area network (WAN) module, or a value added network (VAN) module, but also one of various cable communication modules, such as a universal serial bus (USB), a high definition multimedia interface (HDMI), a digital visual interface (DVI), recommended standard (RS) 232, a power cable, or a plain old telephone service (POTS).

The wired communication module may further include a local interconnect network (LIN) module.

The wireless communication module may include a wireless fidelity (WiFi) module, a wireless broadband (WiBro) module, and/or any wireless communication module for supporting various wireless communication schemes, such as a global system for a mobile communication (GSM) module, a code division multiple access (CDMA) module, a wideband code division multiple access (WCDMA) module, a universal mobile telecommunications system (UMTS), a time division multiple access (TDMA) module, a long-term evolution (LTE) module, etc.

The controller 140 may control an operation of the image obtainer 120 in response to a body scan input received by the inputter 111, process the image obtained by the image obtainer 120, and recognize the body from the processed image and perform a somatotype analysis on the recognized body, and adjust information about the recognized body based on menu information received on the inputter 111 and the analyzed somatotype information.

The controller 140 may generate image information about the changed body image by adjusting information about the body, and control display of a body change image corresponding to the generated image information.

The controller 140 may determine parameters and change values of the body image based on the menu information received by the inputter 111, and may adjust the body image based on the determined parameters and change values of the body image, so that the user can display the actual change in real time.

The controller 140 may adjust the body image based on parameter information of the body corresponding to the somatotype analysis of the user and the change value of the parameter, so that the user can display the actual change in real time.

The controller 140 may include an image processor for image processing the image obtained from the image obtainer 120.

The image processor may analyze the image-processed image, remove a background image from the obtained image, recognize the user's body, and obtain the recognized body information.

Here, obtaining the body information may include obtaining information about a shape of the body, a size of the body, a position of the joints, a size of the joints (width and circumference), and parts of the body, e.g., including the head, neck, arms, hands, elbows, legs, knees, feet, torso, shoulders, chest, abdomen, waist, and pelvis.

The image processor may also adjust the size of the body image obtained by the image obtainer 120 in response to the user's height received by the inputter 111.

The image processor may also change the body image in response to the user input received by the inputter 111. Here, the user input may include selection information of the menu.

As illustrated in FIG. 2, an image processor 140-1 may include a parameter determination module 140*a*, a body image change module 140*b*, and an image viewpoint change module 140*c*.

The configuration of the image processor 140-1 will be described with reference to FIGS. 3, 4, 5A, 5B and 5C.

Figure 3:
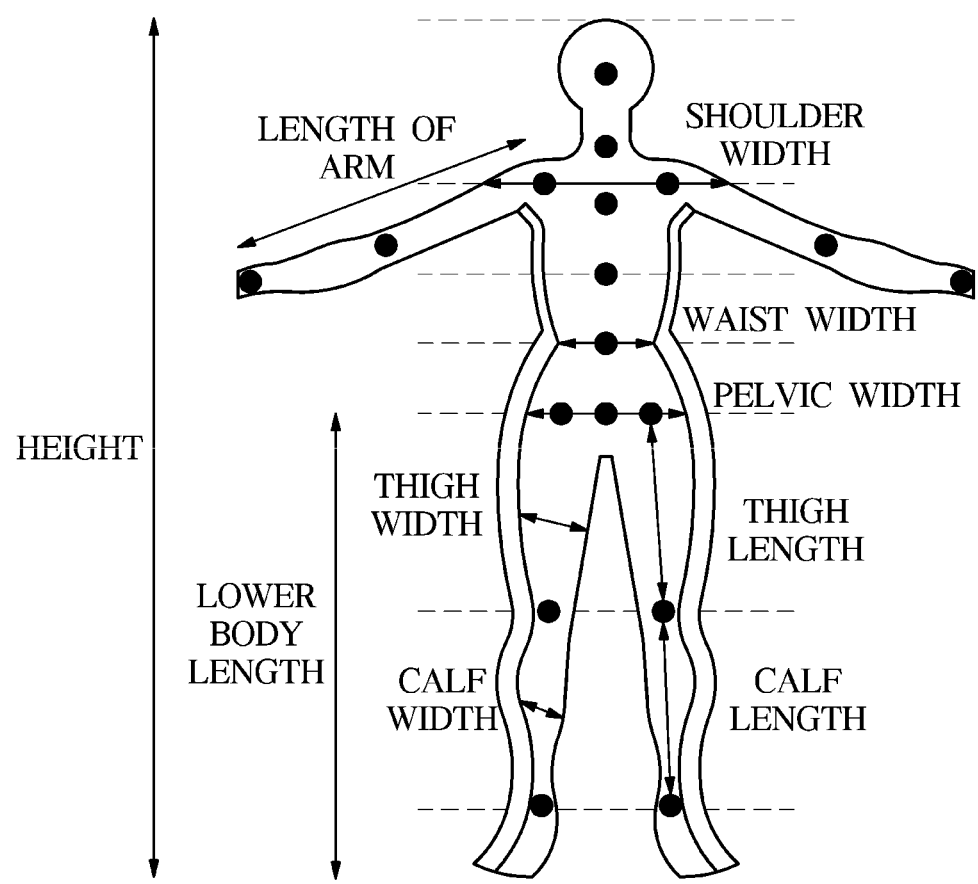
FIG. 3 is an exemplary view of body recognition of a display apparatus according to an embodiment.
Figure 4:
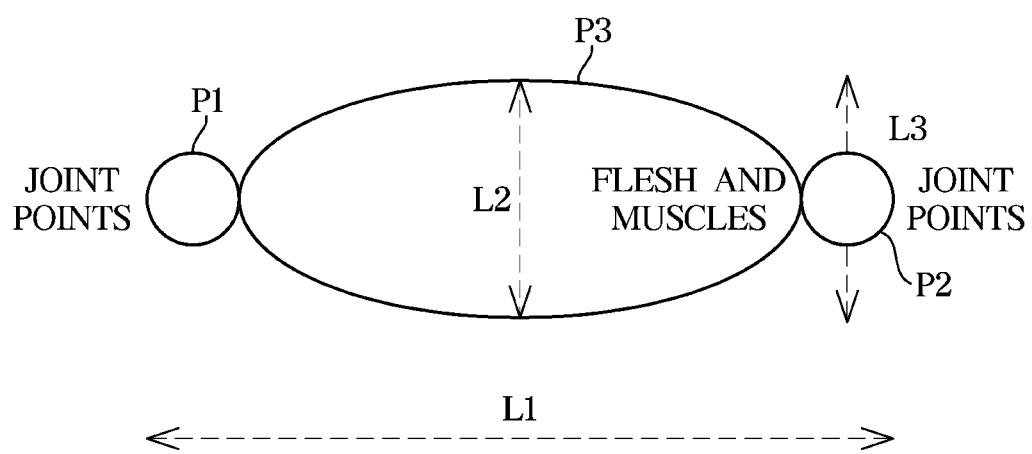
FIG. 4 is an exemplary view of joint recognition of a display apparatus according to an embodiment.
Figure 5A:
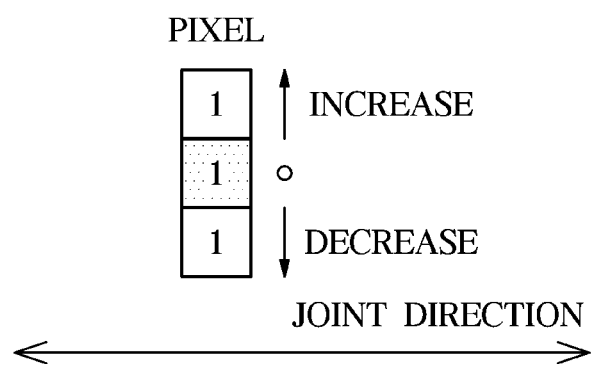
FIGS. 5A, 5B, and 5C are exemplary views of image processing of a display apparatus according to an embodiment.
Figure 5B:
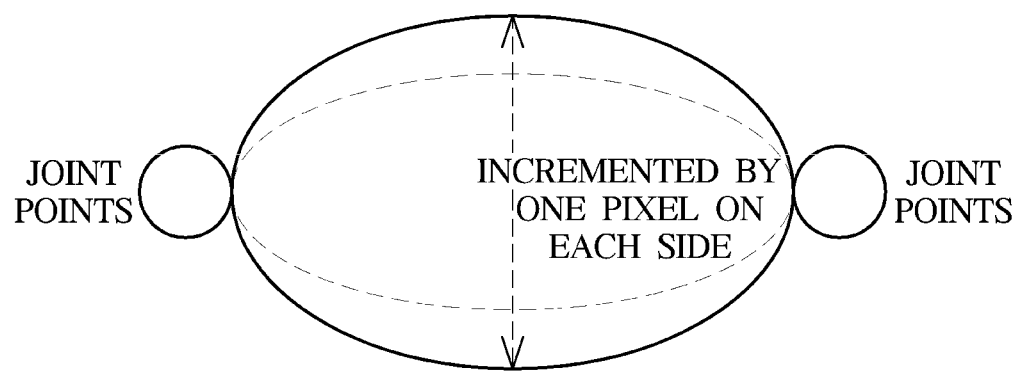
Figure 5C:
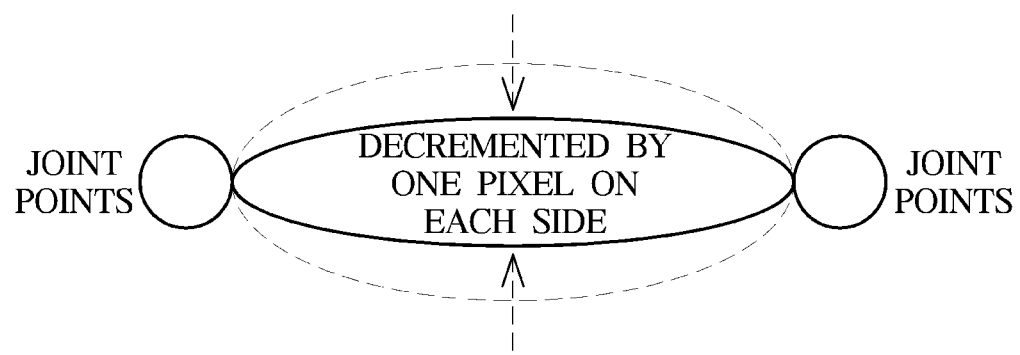

FIG. 3 is an exemplary view of body recognition of a display apparatus according to an embodiment, FIG. 4 is an exemplary view of joint recognition of a display apparatus according to an embodiment, and FIGS. 5A, 5B, and 5C are exemplary views of image processing of a display apparatus according to an embodiment.

The parameter determination module 140*a* may determine a body part whose image is to be changed based on the menu information received by the inputter 111 and the image information of the user's body, obtain a first parameter corresponding to the determined body part, obtain a second parameter based on the menu information received by the inputter 111, and determine a change value to change the first parameter is determined based on the obtained first and second parameters.

The menu may include the somatotype mode, the exercise purpose, and may further include at least one of the exercise type, the exercise intensity, or the exercise time.

The parameters for each body part corresponding to the somatotype mode may include the width, circumference and proportions of the shoulder, waist, and pelvis.

The exercise purpose may include diet, relieving musculoskeletal disease, and building muscle.

The parameters for each body part corresponding to the exercise purpose may include the width, circumference and length of the shoulder, waist, pelvis, arms and legs, and may include inclination values of the neck and shoulders and inclination values of the pelvis.

The parameter determination module 140*a* may obtain the first parameter for each body part, and determine the change value of the first parameter based on the somatotype mode and the exercise purpose.

As illustrated in FIG. 3, the first parameter for each body part may include one or a plurality of waist width, shoulder width, calf width, pelvic width, and thigh width.

The parameter determination module 140*a* may obtain the first parameter for each body part, and determine the change value of the first parameter based on the somatotype mode, the exercise purpose, the exercise type, the exercise intensity, and the exercise time.

The parameter determination module 140*a* may obtain the exercise type, the exercise intensity, and the exercise time based on the somatotype mode and the exercise purpose.

The body image change module 140*b* may change the body image among image information obtained from the image obtainer 120 based on the menu information input to the inputter 111 and parameter information for various parameters.

The body image change module 140*b* may include a joint recognition module b1, a parameter generation module b2, a variable parameter setting module b3, and a body image adjustment module b4.

The joint recognition module b1 may recognize the body in the image obtained from the image obtainer 120, recognize the joint based on the image information on the recognized body, and obtain position information about the recognized joint, and store the obtained position information of the joint.

Referring to FIG. 4, the joint recognition module b1 may articulate based on the image information about the body, recognize joint points that is a center of the joint, and recognize the part between the recognized joint points.

The joint recognition module b1 may analyze the user's somatotype based on the recognized image information about the body and the position information of the joint and store somatotype analysis information for the analyzed somatotype.

The parameter generation module b2 may generate fixed and variable parameters based on the somatotype analysis information and the position information of the joint.

The parameter generation module b2 may subdivide the body into parts based on the image information of the body and pre-stored body skeleton information, and identify joint parts among the subdivided parts.

The parameter generation module b2 may generate a body parameter for the body that does not change even through exercise as a fixed parameter, and generate the body parameter for the body whose width and circumference are changed by muscles according to exercise as a variation parameter.

In other words, the parameter generation module b2 may generate a distance between the user's height and the joints as the fixed parameter, obtain the width and circumference of each joint point, and the width and circumference of a middle point among the parts between the joints, and generate the obtained width and circumference of the middle point among the parts between the joints and the width and circumference of the joint point (i.e., the joint itself) as the variation parameters.

As illustrated in FIG. 4, a distance L1 between a joint point P1 and a joint point P2 may be generated as the fixed parameter, a width L2 of the middle point of a part P3 between the joint point P1 and the joint point P2 may be generated as the variation parameter, and a width L3 of the joint point P2 may also be generated as the variation parameter.

For example, the part between the joints may include biceps, triceps, thigh and calf muscles.

The parameter generation module b2 may generate the width and circumference of the face, neck, belly, hips, and trapezius as the variation parameters.

The parameter generation module b2 may store the generated fixed parameter and variation parameter in the storage 141 as body parameters. In addition, when there are a plurality of users, the storage 141 may store body parameters for each of the plurality of users.

The variable parameter setting module b3 may set maximum and minimum values of the variation parameter corresponding to the somatotype information of the user based on a database DB stored in the storage 141.

Referring to FIG. 4, the variable parameter setting module b3 may set the maximum value and the minimum value at which the width L2 of the middle point of the part P3 between the joint point P1 and the joint point P2 can be changed, and may set the maximum and minimum values at which the width L3 of the joint point P2 can be changed.

Here, the maximum and minimum values of the variation parameters may be set according to the user's body characteristics such as the user's height, lower body length, and arm length.

More particularly, the minimum and maximum values of the variation parameters for the width and circumference of the part between the joints may be identified the minimum and maximum values of the variation parameters of other users having the body information similar to the user among the information stored in the database, and may be set based on statistics of the minimum and maximum values of the variation parameters of other users identified.

The variation parameter may vary depending on the somatotype mode and may be increased or decreased proportionately (increased product) in a current body size.

Since the joint point has less flesh or muscle than the position between the joints, the position between the joint point and the joints may have different weights with increasing proportions of the flesh or muscle. However, unlike the joint points of the arms, legs and neck, in the case of the shoulder and spine, the weight applied to the positions between the joints may be increased proportionately.

The user's body information may include at least one of the user's height, the user's weight, the user's age, or the user's gender, and may also be information received by the inputter 111.

The user's body information may be information obtained based on the body image among the image information obtained from the image obtainer 120.

The body image adjustment module b4 may adjust the size and shape of each part of the body in the body image based on the change value of the parameter determined in the parameter determination module 140a.

The body image adjustment module b4 may adjust the size and shape of each part of the body in the body image based on the change value of the parameter determined in the parameter determination module 140a, the fixed parameter generated in the parameter generation module b2, and the minimum and maximum value of the change parameter set in the variable parameter setting module b3.

That is, the body image adjustment module b4 may adjust the size and shape of each body part in the body image based on the menu information and the parameter information.

The menu information may include information about the somatotype mode and the exercise purpose.

The parameter information may include the change value of the parameter determined in the parameter determination module 140a, the fixed parameter generated in the parameter generation module b2, and the minimum and maximum values of the change parameter set in the variable parameter setting module b3.

The body image adjustment module b4 may also adjust the size and shape of each part of the body in the body image based on the exercise type, the exercise intensity, and the exercise time received by the inputter 111.

The body image adjustment module b4 may perform image processing for each body part based on the parameter information when adjusting the size and shape of each body part in the body image.

That is, when performing image processing for each part of the body based on parameters, the body image adjustment module b4 may select erosion or dilation based on the parameter information, and may adjust the image of a specific body part thick or thin by performing image processing of each part of the body based on the selected erosion or dilation. This will be described with reference to FIGS. 5A, 5B and 5C.

Referring to FIG. 5A, the erosion may be performed when the images of the body parts are arranged perpendicular to a joint direction.

The image processing of erosion may be to decrease the image of the body part by one pixel in a direction perpendicular to the direction of the joint.

The image processing of dilation may be to increase the image of the body part by one pixel in a direction perpendicular to the direction of the joint.

The body image adjustment module b4 may perform image processing of erosion or dilation based on the parameter information, but obtain the number of processing based on the increase or decrease of the body parameter, and perform image processing of the erosion or dilation based on the obtained number of processing.

As illustrated in FIG. 5B, when performing image processing of dilation, the body image adjustment module b4 may adjust the size and shape of each body by increasing the part between the joint point and the joint point by one pixel.

As illustrated in FIG. 5C, when performing image processing of the erosion, the body image adjustment module b4 may adjust the size and shape of each body by decreasing the part between the joint point and the joint point by one pixel.

The image viewpoint change module 140c may receive the body change image and display the received body change image, but change left and right portions of the body change image.

The image viewpoint change module 140c may change the left and right portions of the body image from the viewpoint of the image obtainer 120 (i.e., the camera) to the viewpoint of the user's eye when displaying the realistic image obtained from the image obtainer.

At least one component may be added or deleted corresponding to performance of the components of the image processor 140-1 illustrated in FIG. 2. In addition, it will be readily understood by those skilled in the art that mutual positions of the components may be changed to correspond to performance or structure of a system.

Meanwhile, each component illustrated in FIG. 2 may refer to software and/or hardware components such as a field programmable gate array (FPGA) and an application specific integrated circuit (ASIC).

The controller 140 may perform the parameter determination module 140a, the body image change module 140b, and the image viewpoint change module 140c.

The controller 140 may be provided separately from the image processor 140-1, or may communicate with the image processor 140-1.

The controller 140 may display only an outline of the body change image changed through image processing, or display a silhouette.

The controller 140 may also display the body change image based on a display mode input by the inputter 111.

The display mode may include a nude mode, an all-hidden mode, or a partially hidden mode.

The controller 140 may image-process the body change image based on the reception of the all-hidden mode, and also image-process a preset part based on the reception of the partially hidden mode.

The controller 140 may control an output of request information of a password based on the reception of the nude mode. When the password is received through the inputter 111, the controller 140 may control the display of the body change image in response to the nude mode when the received password is the same as a previously stored password.

The controller 140 may control to output setting request information of the password for displaying the nude mode, and may also store the received password in storage when the password is received through the inputter 111. The controller 140 may also store the received password together with the user's identification information for each user in storage 141.

The controller 140 may also compare the body image of the past with the current body image, check the body part actually converted, and display an image of the body part actually converted.

The controller 140 may compare the past body image with the current body image to identify the body part image actually changed, compare the past body weight with the current body weight to identify the change in weight, and may also output consulting information about the user's somatotype based on the actually changed body part image and weight change.

The consulting information may include guidance information about the part where the body is gaining weight and the part where muscles are weak.

The controller 140 may generate a grid pattern on the body image, extract grid points matching one or more of the user's shoulder, pelvis, and waist from side to side based on a center line in the body image, and extract gradient information of the left grid point and the right grid point of the grid points to recognize the user's balance.

The controller 140 may display a good posture, exercise, food, and the like in the corresponding joint when the result shows that there is a problem in a specific joint through the somatotype analysis of the user.

The controller 140 may also obtain the exercise information for the exercise type, the exercise intensity, and the exercise time corresponding to the user's somatotype analysis information and output the obtained exercise information as recommendation information.

The controller 140 may also output information about the exercise methods for the exercise type selected by the user and the precautions during exercise.

The controller 140 may also function as the image processor 140-1.

The controller 140 may be provided separately from the image processor 140-1. In this case, the controller 140 may communicate with the image processor 140-1.

The storage 141 may store the user's identification information, the user's body information, and the user's body parameters.

The storage 141 may store the password corresponding to the user's identification information and may store information about the user's body image.

The storage 141 may include the database DB for storing the maximum and minimum values of the height, the fixed parameter, and the variation parameter for each somatotype.

The storage 141 may store the body parts for each somatotype mode and the second parameter for each body part.

The storage 141 may store the body parts for each exercise purpose and the second parameter for each body part.

The storage 141 may store the exercise information about the exercise type, the exercise intensity, and the exercise time for each exercise purpose.

The storage 141 may store the guide information such as the exercise methods and precautions for each exercise type.

The storage 141 may delete the stored image according to the control command of the controller 140.

The storage 141 may store basic data for image processing, control data for motion control, and input/output data.

The storage 141 may be configured to store various data for overall operation of the vehicle 1, such as a program for processing or operating the controller 140. The storage 141 may be the memory implemented as a chip separate from the processor associated with the controller 140, and may be implemented as the single chip with the processor.

The storage 141 may be implemented with at least one of a non-volatile memory device, such as a cache, Read Only Memory (ROM), Programmable ROM (PROM), Erasable Programmable ROM (EPROM), and Electrically Erasable Programmable ROM (EEPROM), a volatile memory device, such as Random Access Memory (RAM), or a storage medium, such as Hard Disk Drive (HDD) and Compact Disk (CD) ROM, without being limited thereto.

The display apparatus 1 may further include a sound inputter 150 for receiving sound from the user and surroundings, and a sound outputter 160 for outputting sound of the image displayed on a display 112.

The sound inputter 150 may include at least one microphone or microphone array.

When the sound inputter 150 is provided in the display apparatus 1, the controller 140 may recognize the user's speech based on the sound input by the sound inputter 150 and identify the user input corresponding to the recognized speech.

The sound outputter 160 may output the analysis information about the user's somatotype by the speech, and may output the exercise information by the speech.

The sound outputter 160 may also output a music during the user's exercise time.

The sound outputter 160 may include a speaker. The speaker may convert the amplified low-frequency speech signal into an original sound wave, generate a small wave in an air, and copy the sound wave, thereby outputting audio data as the sound that can be heard by the user.

At least one component may be added or deleted corresponding to performance of the components of the display apparatus 1 illustrated in FIG. 1. In addition, it will be readily understood by those skilled in the art that mutual positions of the components may be changed to correspond to performance or structure of a system.

Figure 7A:
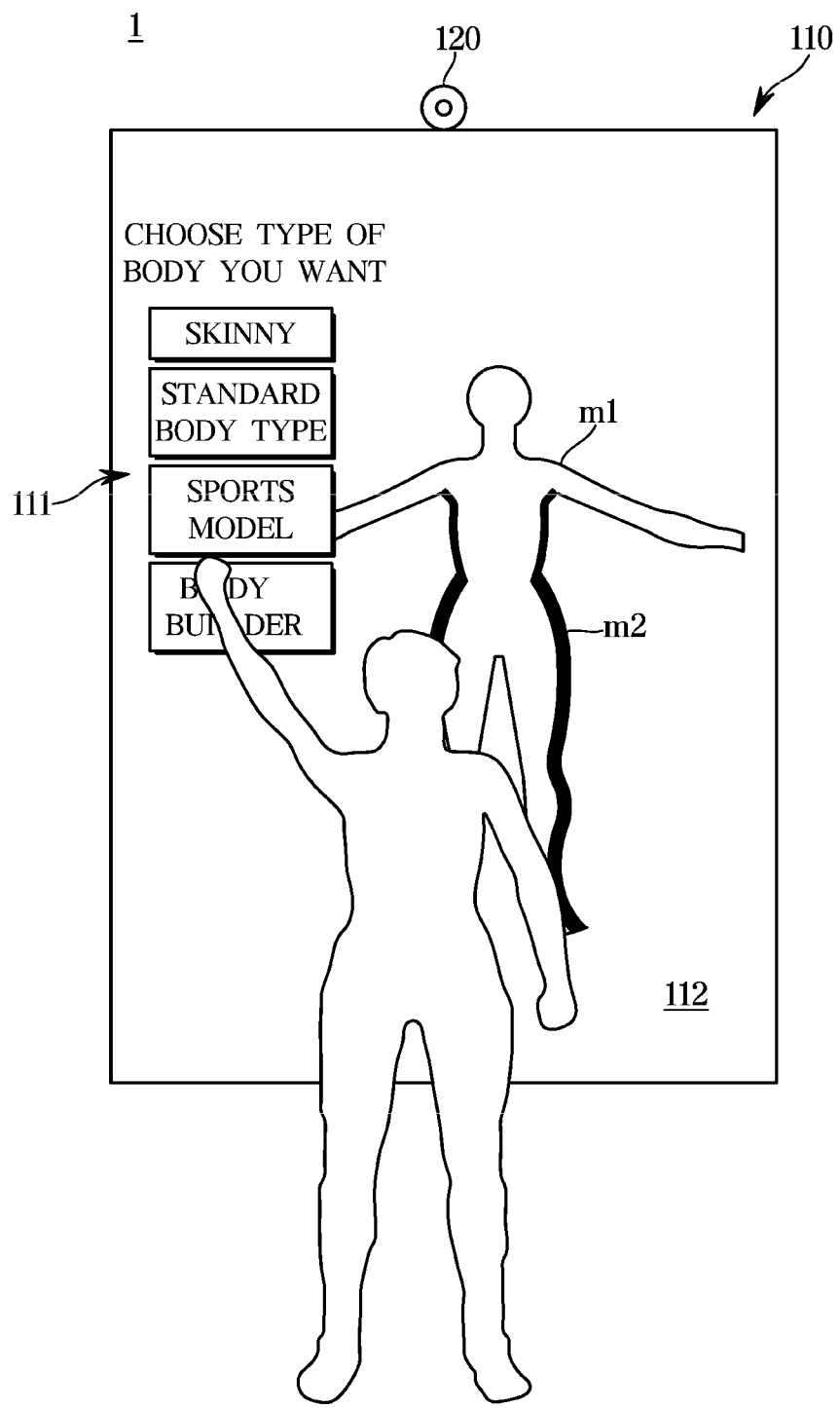
FIGS. 7A, 7B, and 7C are exemplary views of display of a user input of a display apparatus according to an embodiment.
Figure 7B:
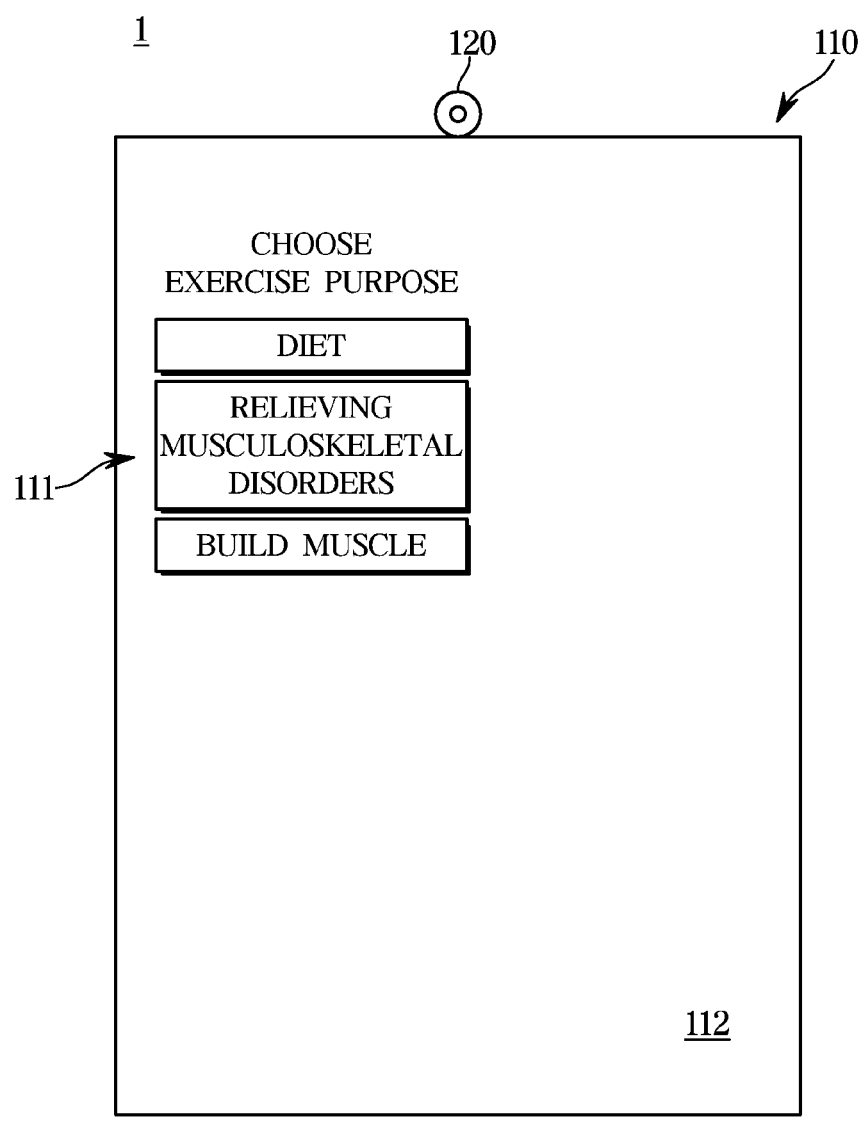
Figure 7C:
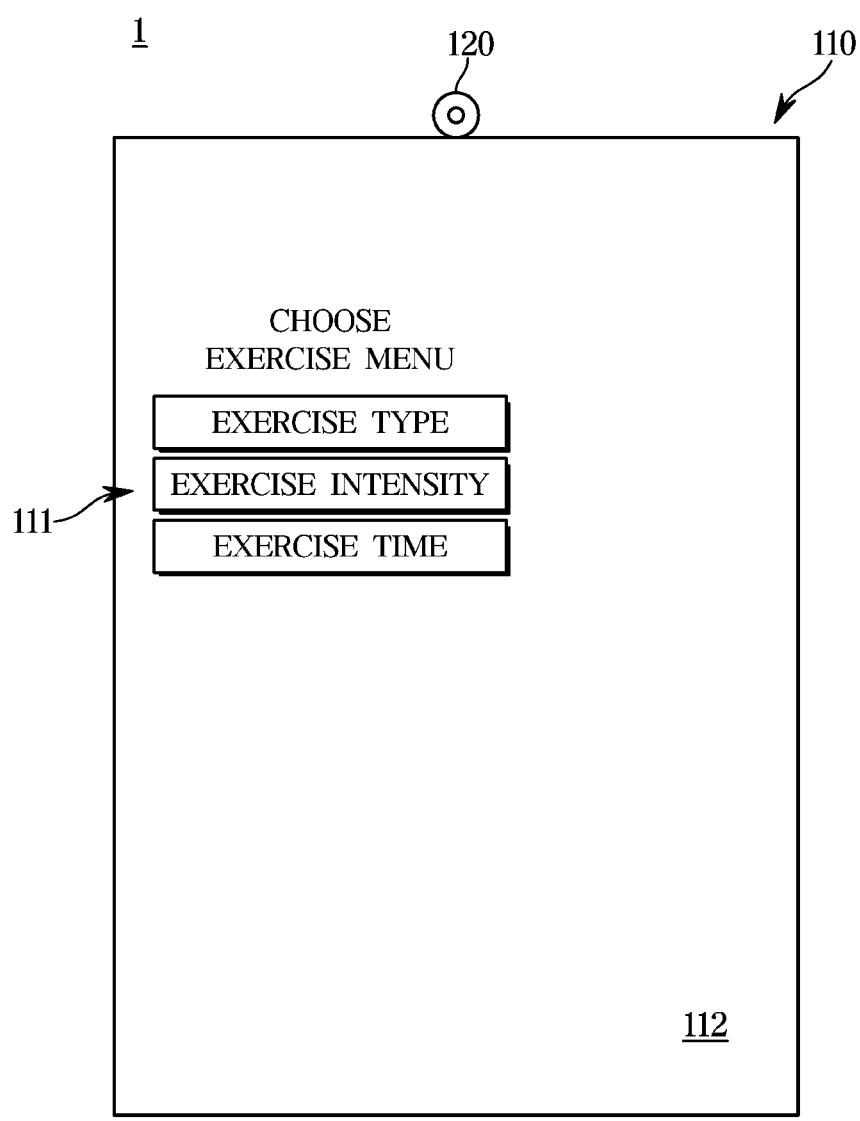

FIG. 6 is a control flowchart of a display apparatus according to an embodiment, and will be described with reference to FIGS. 7A, 7B, and 7C. Here, FIGS. 7A, 7B, and 7C are exemplary views of display of a user input of a display apparatus according to an embodiment.

The display apparatus 1 may obtain the image by operating the image obtainer 120 in response to a body scan command received by the inputter 111 of the user interface 110 (201).

The display apparatus 1 may image-process the image obtained by the image obtainer 120 and recognize the body from the image-processed image (202).

The display apparatus 1 may receive the user input through the inputter 111 of the user interface 110 (203).

Here, the user input may include a command for selecting at least one of a plurality of menus. The menus may include the somatotype mode, the exercise purpose, the guidance of results, and the like.

The somatotype mode is the skinny mode, the standard somatotype mode, the sports model mode, the bodybuilder mode, and the like.

The exercise purpose may include diet, musculoskeletal disease, muscle strengthening, somatotype correction, muscle strength enhancement, muscle endurance enhancement, flexibility enhancement, aerobic enhancement, weight control, cardiovascular health, cancer prevention, bone density loss prevention, diabetes control, psychological benefits, and self-esteem.

The user input may include the exercise type, the exercise intensity, the exercise time, and the like for each exercise purpose.

Referring to FIG. 7A, the display apparatus 1 may display the plurality of somatotype modes through the screen 112. When at least one somatotype mode is selected by the user, the display apparatus 1 may receive the selection signal corresponding to the selected somatotype mode through the inputter 111.

As illustrated in FIG. 7B, the display apparatus 1 may display a plurality of exercise purposes through the screen 112. When at least one exercise purpose is selected by the user, the display apparatus 1 may receive the selection signal corresponding to the selected exercise purpose through the inputter 111.

As illustrated in FIG. 7C, when the selection signal corresponding to the exercise purpose is received, the display apparatus 1 may display buttons for the exercise type, the exercise intensity, and the exercise time selectable by the user through the screen.

The display apparatus 1 may receive the selection signal for the exercise type, the exercise intensity, and the exercise time selected by the user through the inputter 111.

In addition, when the display apparatus 1 displays buttons for the exercise type, the exercise intensity, and the exercise time on the screen, the display apparatus 1 may identify information about the exercise type, the exercise intensity, and the exercise time corresponding to at least one exercise purpose selected by the user, and may display the button with information about the identified exercise type, exercise intensity, and exercise time.

That is, the exercise type, the exercise intensity, and the exercise time selected by the user may be the exercise type, the exercise intensity, and the exercise time for achieving at least one exercise purpose selected by the user.

The display apparatus 1 may determine the body part image to be changed based on the user input received by the inputter 111 and the image information of the user's body, obtain the first parameter corresponding to the determined body part, obtain the second parameter based on the user input received by the inputter 111, and determine the change value to change the first parameter based on the obtained first and second parameters (204).

Here, the user input may include at least one somatotype mode and at least one exercise purpose.

The parameter for each body part corresponding to the somatotype mode may include the width, circumference, and proportions of the shoulder, waist, and pelvis.

The exercise purpose may include diet, relieving musculoskeletal disease, and building muscle.

The parameter for each body part corresponding to the exercise purpose may include the width, circumference and length of the shoulder, waist, pelvis, arms and legs, and may include the inclination values of the neck and shoulders and the inclination values of the pelvis.

The first parameter for each body part may include one or the plurality of waist width, shoulder width, calf width, pelvic width, and thigh width.

The display apparatus 1 may recognize the joint based on the image information about the body, and obtain the position information about the recognized joint.

The display apparatus 1 may articulate based on the image information about the body, recognize the joint point that is the center of the joint, and recognize the part between the recognized joint points.

The display apparatus 1 may analyze the user's somatotype based on the image information about the body and the position information of the joint.

The display apparatus 1 may generate the fixed and variation parameters based on the somatotype analysis information and the joint position information. Here, the fixed parameter may be the body parameter for the body that does not change through exercise, and the variation parameter may be the body parameter for the body whose width and circumference are changed by muscles according to exercise.

In other words, the display apparatus 1 may generate a distance between the user's height and the joints as the fixed parameter, obtain the width and circumference of each joint point, and the width and circumference of a middle point among the parts between the joints, and generate the obtained width and circumference of the middle point among the parts between the joints and the width and circumference of the joint point (i.e., the joint itself) as the variation parameters.

The display apparatus 1 may set the maximum and minimum values of the variation parameter corresponding to the somatotype information of the user based on the database DB stored in the storage 141 (205).

The display apparatus 1 may set the maximum value and the minimum value at which the width L2 of the middle point of the part P3 between the joint point P1 and the joint point P2 can be changed, and may set the maximum and minimum values at which the width L3 of the joint point P2 can be changed.

Here, the maximum and minimum values of the variation parameters may be set according to the user's body characteristics such as the user's height, lower body length, and arm length.

More particularly, the minimum and maximum values of the variation parameters for the width and circumference of the part between the joints may be identified the minimum and maximum values of the variation parameters of other users having the body information similar to the user among the information stored in the database, and may be set based on statistics of the minimum and maximum values of the variation parameters of other users identified.

The display apparatus 1 may change the size and shape of each body part in the body image based on the determined change value of the parameter, the generated fixed parameter, and the minimum and maximum values of the set change parameter (206).

More particularly, when performing image processing for each part of the body based on the parameter information, the display apparatus 1 may select erosion or dilation based on the parameter information, and may adjust the image of a specific body part thick or thin by performing image processing of each part of the body based on the selected erosion or dilation.

The image processing of erosion may be to decrease the image of the body part by one pixel in a direction perpendicular to the direction of the joint. The image processing of dilation may be to increase the image of the body part by one pixel in a direction perpendicular to the direction of the joint.

The display apparatus 1 may obtain the increase or decrease of the body parameter based on the parameter information, obtain the number of processing based on the increase or decrease of the body parameter, and perform image processing of the erosion or dilation based on the obtained number of processing.

When performing image processing of dilation, the display apparatus 1 may adjust the size and shape of each body by increasing the part between the joint point and the joint point by one pixel.

When performing image processing of the erosion, the display apparatus 1 may adjust the size and shape of each body by decreasing the part between the joint point and the joint point by one pixel.

The display apparatus 1 may change the left and right portions of the body change image and display the body change image whose left and right portions are changed (207). That is, the display apparatus 1 may change the left and right portions of the body image to be the viewpoint of the user's eye from the viewpoint of the image obtainer 120 (i.e., the camera).

The display apparatus 1 may display a somatotype model selected by the user and change in the body image in real time depending on the exercise purpose.

The display apparatus 1 may display changes in the body image in real time depending on the exercise time or the exercise intensity selected by the user.

At this time, the user may determine the necessary exercise information by real-time identifying the part that can change (m1→m2 in FIG. 7A) according to various menus based on his somatotype, thereby designing a customized somatotype exercise.

Figure 8:
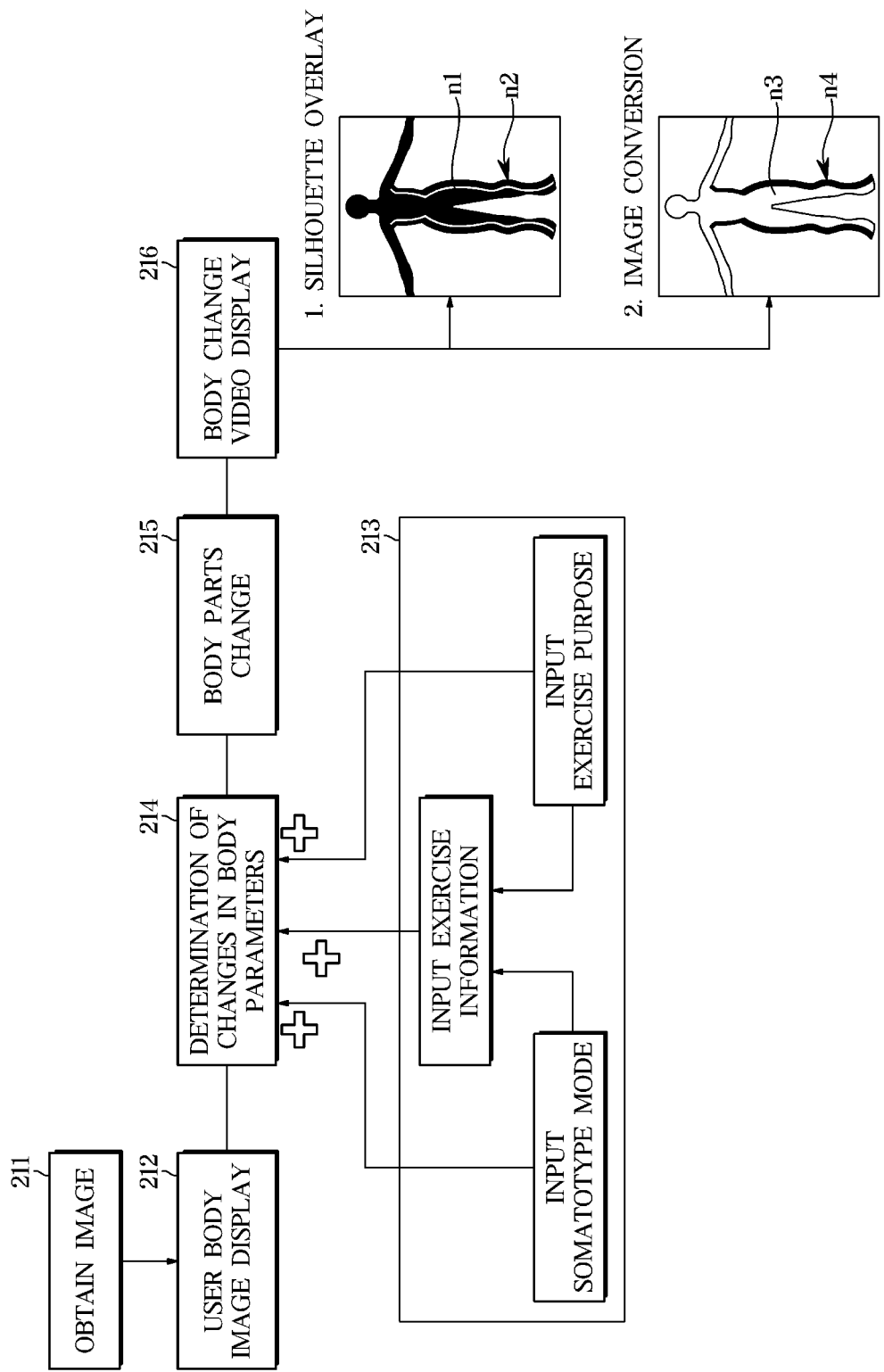
FIG. 8 is a control flowchart of a display apparatus according to another embodiment.

FIG. 8 is a control flowchart of a display apparatus according to another embodiment. The display apparatus 1 may obtain the image by operating the image obtainer 120 in response to the body scan command received by the inputter 111 (211).

The display apparatus 1 may image-process the image obtained by the image obtainer 120, recognize the body from the image-processed image, and display the image of the recognized user's body (212).

The display apparatus 1 may receive the user input through the inputter 111 of the user interface 110 (203). The display apparatus 1 may receive the somatotype mode, the exercise purpose, and the exercise information.

The display apparatus 1 may determine the body part image to be changed based on the somatotype mode, the exercise purpose, and the exercise information received by the inputter 111, and obtain the first parameter that is the user's body parameter for the determined body part.

The display apparatus 1 may obtain the second parameter that is a reference parameter for the body part determined based on the somatotype mode, the exercise purpose, and the exercise information received by the inputter 111.

The display apparatus 1 may determine the change value to change the first parameter based on the first parameter and the second parameter (214).

The display apparatus 1 may change the image for the determined body part by applying the change value to the determined body part among the user's body images (215), and display the changed body change image (216).

The display apparatus 1 may display an original body image n1 by overlaying the image of the changed part. That is, the display apparatus 1 may display a silhouette n2 overlaid on the user's original body image n1.

The display apparatus 1 may display the corrected body image by correcting the image of the changed part in an original body image n3. That is, the display apparatus 1 may display a correction image n4 that corrects the user's original body image n3.

According to the embodiments of the disclosure, the disclosure may provide the user with a desired somatotype by providing the user with the exercise information corresponding to the user's current somatotype and user needs. Accordingly, the user's satisfaction may be improved.

The disclosure automatically obtains joint points and displays body changes based on the extracted joint points, thereby increasing the accuracy of body changes without requiring a separate manpower and conveniently and efficiently analyzing the user's somatotype in a narrow space.

The disclosure may improve the user's perception of body changes and increase convenience by displaying the user's body changes according to the user's view.

The disclosure may provide necessary exercise information to the user through somatotype analysis of the user. This allows the user to design a somatotype-specific exercise. In addition, the user may identify a part that can be changed according to various menus on the screen in real time based on the somatotype.

The disclosed embodiments may be implemented in the form of a recording medium storing computer-executable instructions that are executable by a processor. The instructions may be stored in the form of a program code, and when executed by a processor, the instructions may generate a program module to perform operations of the disclosed embodiments. The recording medium may be implemented non-transitory as a computer-readable recording medium.

The non-transitory computer-readable recording medium may include all kinds of recording media storing commands that can be interpreted by a computer. For example, the non-transitory computer-readable recording medium may be, for example, ROM, RAM, a magnetic tape, a magnetic disc, flash memory, an optical data storage device, etc.

Embodiments of the disclosure have thus far been described with reference to the accompanying drawings. It should be obvious to a person of ordinary skill in the art that the disclosure may be practiced in other forms than the embodiments as described above without changing the technical idea or essential features of the disclosure. The above embodiments are only by way of example, and should not be interpreted in a limited sense.

What is claimed is:

1. A display apparatus comprising:
a communicator configured to receive image information about an image obtained by an image obtainer;
an inputter configured to receive menu information of at least one of a somatotype mode or an exercise purpose;
a storage configured to store information about maximum and minimum values of variation parameters for each fixed parameter and a height of a user,
a controller configured to:
obtain a body image of the user based on the image information received by the communicator,
recognize joints based on the obtained body image,
obtain position information of the recognized joints based on the obtained body image,
obtain a first parameter tor each part of a body of the user based on the obtained position information of the joints,
obtain a second parameter for each part of the body of the user corresponding to the somatotype mode and the exercise purpose received by the inputter,
determine a change value of the parameter for each part of the body of the user based on the obtained first and second parameters for each part of the body of the user,
generate a distance between the recognized joints as a fixed parameter, generate a width and circumference of the part between the recognized joints and a width and circumference of the joints as variation parameters, obtain the maximum and minimum values of the variation parameters based on the information stored in the storage and body information of the user, obtain an increase or decrease of the first parameter for each pan of the body of the user based on the determined change value of the parameter for each part of the body of the user and the maximum and minimum values of the obtained variation parameters, perform erosion image processing or dilation image processing for each part of the body of the user based on the obtained increase or decrease of the first parameter for each part of the body of the user, change an image for each part of the body by the erosion image processing or the dilation image processing for each part of the body of the user; and a screen configured to display the changed image in response to a control command of the controller.

2. The display apparatus according to claim 1, wherein the controller is configured to:
   identify the number of pixels corresponding to the increase or decrease of the first parameter for each part of the body of the user; and
   perform erosion image processing or dilation image processing for each part of the determined body based on the identified number of pixels.

3. The display apparatus according to claim 2, wherein the controller is configured to perform the erosion image processing or the dilation image processing in a direction perpendicular to a direction in which the joints are connected.

4. The display apparatus according to claim 1, wherein the controller is configured to:
   generate a body change image reflecting the changed image of each part of the body;
   change left and right portions of the generated body change image; and
   control the screen to display the body change image with the left and right portions changed.

5. The display apparatus according to claim 4, wherein the controller is configured to control the screen to display the obtained body image and the body change image in an overlaid manner.

6. The display apparatus according to claim 1, wherein:
   the inputter is configured to receive at least one exercise information among an exercise type, an exercise time, or an exercise intensity; and
   the controller is configured to adjust at least one of the obtained parameters for each part of the body based on the received exercise information.

7. The display apparatus according to claim 1, wherein the image obtainer is integrally provided with the screen.

8. The display apparatus according to claim 1, wherein:
   the inputter comprises a touch panel; and
   the screen comprises a display panel provided on one side of the touch panel.

9. A method of controlling a display apparatus comprising:
   obtaining image information using an image obtainer;
   obtaining body images of a user based on the received image information;
   recognizing joints based on the obtained body image,
   obtaining position information of the recognized joints based on the obtained body image,
   obtaining a first parameter for each part of a body of the user based on the obtained position information of the joints,
   obtaining a second parameter for each part of the body of the user corresponding to the somatotype mode and the exercise purpose received by an inputter,
   determining a change value of the parameter for each part of the body of the user based on the obtained first and second parameters for each part of the body of the user,
   generating a distance between the recognized joints as a fixed parameter,
   generating a width and circumference of the part between the recognized joints and a width and circumference of the joints as variation parameters,
   obtaining maximum and minimum values of the variation parameters based on information stored in a storage and body information of the user,
   obtaining an increase or decrease of the first parameter for each part of the body of the user based on determined change value of the parameter for each part of the body of the user and the maximum and minimum values of the obtained variation parameters,
   performing erosion image processing or dilation image processing for each part of the body of the user based on the obtained increase or decrease of the first parameter for each part of the body of the user,
   changing an image for each part of the body by the erosion image processing or the dilation image processing for each part of the body of the user; and
   displaying changed image through a screen,
   wherein the information stored in the storage comprises information about maximum and minimum values of the variation parameters for each fixed parameter and a height of the user.

10. The method according to claim 9, wherein the performing of the erosion image processing or the dilation image processing for each part of the determined body comprises:
    identifying the number of pixels corresponding to the increase or decrease of the first parameter for each part of the user's body; and
    performing the erosion image processing or the dilation image processing for each part of the determined body based on the identified number of pixels, but performing the erosion image processing or the dilation image processing in a direction perpendicular to a direction in which the joints are connected.

11. The method according to claim 9, further comprising:
    generating a body change image reflecting the changed image of each part of the body;
    changing left and right portions of the generated body change image; and
    controlling the screen to display the body change image with the left and right portions changed on the obtained body image.

12. The method according to claim 9, further comprising:
    when at least one exercise information among an exercise type, an exercise time, or an exercise intensity is received through the inputter, adjusting at least one of the obtained parameters for each part of the body based on the received exercise information.

* * * * *